United States Patent
Gross et al.

(10) Patent No.: US 10,130,113 B2
(45) Date of Patent: Nov. 20, 2018

(54) COMPOSITION AND METHOD FOR PROVIDING GLUTAMINE

(75) Inventors: Kathy Gross, Topeka, KS (US); Christina Khoo, Pembroke, MA (US)

(73) Assignee: Colgate-Palmolive Company, New York, NY (US)

( * ) Notice: Subject to any disclaimer, the term of this patent is extended or adjusted under 35 U.S.C. 154(b) by 1507 days.

(21) Appl. No.: 11/917,109

(22) PCT Filed: Jun. 9, 2006

(86) PCT No.: PCT/US2006/022458
§ 371 (c)(1),
(2), (4) Date: Jul. 8, 2008

(87) PCT Pub. No.: WO2006/135736
PCT Pub. Date: Dec. 21, 2006

(65) Prior Publication Data
US 2009/0215900 A1    Aug. 27, 2009

Related U.S. Application Data

(60) Provisional application No. 60/689,126, filed on Jun. 9, 2005.

(51) Int. Cl.
| | | |
|---|---|---|
| A23K 20/147 | (2016.01) | |
| A23K 10/20 | (2016.01) | |
| A23K 50/48 | (2016.01) | |
| A23K 20/142 | (2016.01) | |
| A23K 20/163 | (2016.01) | |
| A23L 33/00 | (2016.01) | |
| A23L 33/18 | (2016.01) | |

(52) U.S. Cl.
CPC ............ *A23K 10/20* (2016.05); *A23K 20/142* (2016.05); *A23K 20/147* (2016.05); *A23K 20/163* (2016.05); *A23K 50/48* (2016.05); *A23L 33/18* (2016.08); *A23L 33/40* (2016.08)

(58) Field of Classification Search
None
See application file for complete search history.

(56) References Cited

U.S. PATENT DOCUMENTS

| | | | | |
|---|---|---|---|---|
| 3,115,409 A | * | 12/1963 | Hallinan ................. | A23K 10/26 426/641 |
| 4,015,026 A | | 3/1977 | Burkwall, Jr. et al. | |
| 4,160,038 A | * | 7/1979 | Groben .................. | A23K 50/45 426/335 |
| 4,879,131 A | | 11/1989 | de Rahm | |
| 5,039,532 A | | 8/1991 | Jost et al. | |
| 5,456,934 A | * | 10/1995 | Lee et al. ....................... | 426/549 |
| 5,589,357 A | | 12/1996 | Martinez et al. | |
| 5,849,335 A | | 12/1998 | Ballevre et al. | |
| 6,403,142 B1 | | 6/2002 | McDaniel, III et al. | |
| 6,455,273 B1 | | 9/2002 | Kodera et al. | |
| 6,582,740 B1 | | 6/2003 | May et al. | |
| 6,589,574 B2 | | 7/2003 | Swamylingappa et al. | |
| 2003/0032583 A1 | * | 2/2003 | Ostrom ................ | A61K 38/011 514/5.5 |
| 2003/0035882 A1 | | 2/2003 | McDaniel, III et al. | |
| 2003/0134851 A1 | * | 7/2003 | Baxter et al. .............. | 514/231.2 |
| 2003/0162723 A1 | | 8/2003 | Harris et al. | |
| 2005/0031673 A1 | | 2/2005 | Saylock et al. | |
| 2005/0107303 A1 | * | 5/2005 | Butterwick et al. ............ | 514/17 |

FOREIGN PATENT DOCUMENTS

| | | | |
|---|---|---|---|
| CA | 2259410 | 2/1998 | |
| CA | 2308348 | 4/2000 | |
| EP | 0 540 462 A | 5/1993 | |
| EP | 0672352 B1 * | 9/2002 | ............... A23J 3/34 |
| EP | 0672352 B1 | 9/2002 | |
| EP | 1236405 B1 | 6/2006 | |
| JP | 07-255398 | 10/1995 | |
| JP | 10-139681 | 5/1998 | |
| JP | 2002-223732 | 8/2002 | |
| JP | 2004 051494 A | 2/2004 | |
| WO | WO 03/053159 | 7/2003 | |

OTHER PUBLICATIONS

Mayabb Technical Report, Wheat gluten, 2007) (available at http://www.royalcanin.us/library/ingredients-nutrients-wheat-gluten-in-pet-food.aspx).*
Neilly, P.J.D. et al., "Topical Glutamine Therapy in Experimental Inflammatory Bowel Disease," Clinical Nutrition, (1995) p. 283, paragraph 2—p. 284, paragraph 2, vol. 14 XPOO4680204.
Newsholme, E.A., "The Importance of Glutamine in Nutrition of the Immune System," Clinical Nutrition, (1995), pp. 129-130, XP004680284—vol. 14, The Whole Document is Relevant.
Search Report from the European Patent Office dated Nov. 14, 2008 for corresponding EP Patent Application No. EP 06772673.
Daminet, 1996, "Gluten-Sensitive Enteropathy in a Family of Irish Setters," Can. Vet. J. 37(12):745-746.
Guilford, 1994, "Nutritional Management of Gastrointestinal Tract Diseases of Dogs and Cats," J. Nutrition 124(12 Suppl.):2663S-2669S.
International Search Report and Written Opinion in International Application No. PCT/US06/022458, dated Oct. 16, 2006.

* cited by examiner

*Primary Examiner* — H. Sarah Park

(57) ABSTRACT

A process for preparing a glutamine-supplemented food product by contacting water and a nutritive base that predominantly comprises meat and carbohydrate with a peptide source of glutamine to form a wet mixture and heating the wet mixture at a temperature of from about 50° C. to about 105° C. for a time sufficient to cook the nutritive base. The process forms a cooked food composition comprising from about 60% to about 85% by weight water. The product is useful for feeding to an animal to increase glutamine absorption or to strengthen immune function.

25 Claims, No Drawings

COMPOSITION AND METHOD FOR PROVIDING GLUTAMINE

CROSS-REFERENCE TO RELATED APPLICATIONS

This application claims priority to U.S. Provisional Application Ser. No. 60/689,126 filed Jun. 9, 2005, the disclosure of which is incorporated herein by reference.

FIELD OF THE INVENTION

The invention relates generally to nutritional compositions and particularly to nutritional food compositions comprising supplemental glutamine and to methods for preparing and using such compositions.

BACKGROUND OF THE INVENTION

Glutamine can be synthesized by various tissues such as skeletal muscles, liver, and adipose tissue. However, research indicates that glutamine is conditionally essential when the metabolic demand for glutamine exceeds the amount available in the free glutamine pool and that which can be provided by de novo synthesis. For example, during exercise or other times of metabolic stress (e.g. fasting, severe injury, illness, etc.), the demand for plasma glutamine markedly increases. For instance, various cells of the immune system such as the lymphocytes and macrophages depend on glutamine as a primary fuel source, and thus the demand for glutamine increases when an immunological response is mounted.

Methods for using glutamine have been described in the art. European Patent No. 672 352 describes various solutions containing a glutamine-rich peptide preparation. U.S. Pat. No. 5,849,335 proposes a composition and method for providing glutamine to a human or animal using carob germ protein hydrolysate.

Despite the availability of free glutamine (L-glutamine), supplementation of foods with free glutamine has a number of limitations. For example, free glutamine is unstable at high temperatures or under certain conditions associated with food processing. Compositions comprising free glutamine cannot be sterilized or further processed at high temperature and/or high pressure, for example, in the form of a canned food, without destroying the free glutamine. There is, therefore, a need for nutritional food compositions that provide supplemental glutamine.

SUMMARY OF THE INVENTION

The present invention provides a retortable cooked food composition comprising water in an amount of from about 60% to about 85% by weight, a nutritive base that predominantly comprises meat and carbohydrate, and a peptide source of glutamine.

The invention also provides a glutamine-supplemented food product comprising a sealed retortable container containing such a food composition.

The invention further provides a process for preparing such a glutamine-supplemented food product. The process comprises (a) contacting water and a nutritive base that predominantly comprises meat and carbohydrate with a peptide source of glutamine to form a wet mixture; (b) heating the wet mixture at a temperature of from about 50° C. to about 105° C. for a time sufficient to cook the nutritive base, to form a cooked food composition comprising from about 60% to about 85% by weight water; (c) packaging the cooked food composition in a sealed retortable container; and (d) sterilizing the packaged composition by a retort procedure to form the food product.

The invention also provides a method for increasing glutamine absorption in an animal. The method comprises feeding the animal a cooked food composition comprising water in an amount of from about 60% to about 85% by weight, a nutritive base that predominantly comprises meat and carbohydrate, and a peptide source of glutamine.

The invention additionally provides a method for strengthening immune function of an animal in need thereof. The method comprises maintaining the animal, for an immune function strengthening effective period, on a dietary ration that comprises at least one cooked food composition comprising water in an amount of from about 60% to about 85% by weight, a nutritive base that predominantly comprises meat and carbohydrate, and a peptide source of glutamine.

Other and further objects, features, and advantages of the present invention will be readily apparent to those skilled in the art.

DETAILED DESCRIPTION OF THE INVENTION

In one aspect, the invention provides food compositions comprising a source of glutamine that remains stable under processing conditions of high temperature and/or pressure such as those typically associated with preparing a canned food composition. The invention is based in part on a finding that adding a peptide source of glutamine to a high moisture-content meat and carbohydrate based food composition, before high temperature and/or high pressure processing to cook and/or sterilize the food, results in the glutamine being more stable than compositions wherein free glutamine is used in place of the peptide source, yet remaining readily bioavailable to an animal consuming the food. On heating, free glutamine readily degrades to glutamate, with release of ammonia, which can be toxic. A more stable glutamine source, as described herein, thus overcomes at least two problems in a cooked food product: loss of glutamine, and possible accumulation of ammonia.

The food composition is described herein as "retortable." A "retortable" food composition is one that is ready for placement in a sealed container or already in such a container, the composition being suitable for sterilization, for example, by subjecting the composition to high heat and/or pressure as in a retort procedure, or already subjected to such a sterilization process, as commonly used, for example, to sterilize canned food products. A "retortable" container is a container suitable for use under heat or heat and pressure as in, for example, a sterilization process, and is most commonly a sealable or sealed metal can or foil pouch.

Use of other means for sterilizing the food composition, including thermal or non-thermal sterilization, aseptic processing, ultra heat treatment (UHT), and/or high pressure, does not of itself remove a composition from the present scope, so long as the composition is one that could, if desired, be sterilized by a retort procedure without substantial loss of physical or chemical integrity or acceptability for consumption by an animal.

The food composition is further described herein as "cooked." Cooking has various effects on a meat and carbohydrate based food, including tenderizing (e.g., by protein denaturation) and/or browning of the meat component, and softening, swelling and/or gelatinization of the carbohydrate component, that will be readily evident on cursory examination of the composition. The method and conditions of cooking are not critical with respect to the present composition, but illustratively can be as described herein according to a process embodiment of the invention. However, it will be understood that, as described herein, the entire composition, including the peptide source component, is a "cooked" composition, i.e., cooking occurs after addition of the peptide source of glutamine to the nutritive base.

The food composition is of a type known as a "wet" or "moist" food in the animal nutrition arts, typically comprising from about 60% to about 85% by weight water, i.e., having a dry matter (DM) content of from about 15% to about 40% by weight. In one embodiment, the mixture comprises from about 65% to about 80% by weight water, for example, about 75% by weight water.

The bulk of the dry matter in a food composition of the invention is a "nutritive base," which comprises basic food ingredients that supply, at least in part, an animal's dietary requirements of metabolizable energy (ME) and protein, and optionally other essential nutrients such as essential amino acids, essential fatty acids, vitamins and minerals. The nutritive base predominantly comprises (i.e., in an amount greater than 50% by weight) a meat component and a carbohydrate component. In a particular embodiment, a meat and carbohydrate component may comprise more than about 75% by weight of the nutritive base.

The meat component can be derived from any one or more animal (e.g., mammal, bird, fish or seafood) proteinaceous tissue including muscle tissue and/or offal, and can be in any physical form, for example readily identifiable pieces or chunks, or in minced, ground or reconstituted form.

The carbohydrate component can comprise starches, sugars and/or celluloses and is most typically derived from grains (e.g., wheat, corn, rice, etc.), legumes (e.g., soy), tubers (e.g., potato) and/or other carbohydrate-rich plant parts (e.g., beet pulp, sago, tapioca, etc.). The carbohydrate component can be in whole form (e.g., whole grains) or in ground or milled form (e.g., wheat flour, milled oat bran).

The nutritive base optionally comprises a fat or oil component and/or a fiber component. In one embodiment the nutritive base provides a substantially nutritionally complete dietary ration for an animal. A "nutritionally complete" dietary ration is one that includes sufficient nutrients for maintenance of normal health of a healthy animal maintained on the dietary ration. In another embodiment the nutritive base requires supplementation with additional nutrients such as essential amino acids, essential fatty acids, vitamins and minerals to provide a nutritionally complete diet.

The food composition comprises at least one peptide source of glutamine. As used herein, a peptide source of glutamine contains polypeptide fragments of various amino acid chain lengths, including oligopeptides, tripeptides and dipeptides, and in some cases free amino acids. In one embodiment, the peptide source of glutamine comprises a protein hydrolysate that comprises stable glutamine. The hydrolysate can serve as a source of general protein nutrition as well as a source of specific amino acids including glutamine. As used herein, "hydrolysate" refers to a product of hydrolysis of a protein source or a synthetic equivalent of such a product, regardless of the particular process by which it is made. The hydrolysate can be relatively homogeneous or heterogeneous in amino acid chain length.

Polypeptides and fragments thereof, including free amino acids, in the peptide source can have a range of molecular weights such that, for example, at least about 99% by weight of such polypeptides and fragments have a molecular weight of less than about 50 kd (kilodaltons). In one embodiment, no more than about 10% by weight have a molecular weight of about 10 kd or greater. In various embodiments the weight average molecular weight of the polypeptides and fragments thereof in the peptide source is no greater than about 18 kd, no greater than about 12 kd, no greater than about 10 kd, no greater than about 8 kd, no greater than about 6 kd, no greater than about 4 kd, or no greater than about 2 kd.

Molecular weight of a component of a peptide source, including an average molecular weight such as a weight average molecular weight, can be determined using any method known to skilled artisans. For example, molecular weight distribution of polypeptides and fragments thereof in a protein hydrolysate can be determined using size exclusion chromatography in a medium such as Sephadex® (Pharmacia), or by gel electrophoresis, for example, using SDS-polyacrylamide gel electrophoresis.

The peptide source can further comprise other chemical substances in addition to polypeptides, amino acid chain fragments and free amino acids, such as, for example, lipids, fats, oils, vitamins and carbohydrates. The peptide source can comprise components derived from the biological material used to generate the peptide source, and/or chemical substances added by a peptide source manufacturer. These substances can be, for example, a carbohydrate such as sucrose, tapioca starch, corn sweetener, cornstarch, a partially hydrolyzed starch, cellulose, or partially hydrolyzed cellulose. Other non-limiting examples of components that can be present in a peptide source include organic oils, such as soybean oil, safflower oil, palm oil, coconut oil, sunflower oil, peanut oil or canola oil.

In certain embodiments, the peptide source of glutamine can comprise a protein hydrolysate derived from a plant (i.e., a plant protein hydrolysate) or an animal (i.e., an animal protein hydrolysate).

A plant protein hydrolysate can be, without limitation, a hydrolysate of protein obtained from edible tissue of, for example, a crop, a grain, a fruit, a root, a tuber, a stem, a leaf, a vegetable, or any combination thereof. In one embodiment, the protein hydrolysate is derived at least in part from seeds or grains of crops such as barley, oat, rye, triticale, wheat (including bread wheat, durum wheat, Kamut® wheat and spelt), soy, and combinations thereof. Specific examples of useful plant protein hydrolysates include soy gluten hydrolysate, wheat gluten hydrolysate, and combinations thereof.

An animal protein hydrolysate can be, without limitation, a hydrolysate of protein obtained from tissue of a mammal, a bird, a reptile, an amphibian, a fish, an invertebrate, or any combination thereof. Examples of mammalian protein sources include cattle, sheep, pig, goat, deer, rabbit, horse and kangaroo, in particular their milk, curds, whey, blood, and internal tissues and organs such as smooth muscle, striate muscle, liver, kidney, intestine and heart. Examples of avian protein sources include chicken, turkey, goose, duck, ostrich, quail and pigeon, in particular their eggs and internal tissues and organs such as smooth muscle, striate muscle, liver, kidney, intestine and heart. Examples of reptilian protein sources include alligator, lizard, turtle and snake. Examples of amphibian protein sources include frog and salamander. Examples of fish protein sources include catfish, herring, salmon, tuna, bluefish, cod, halibut, trout, swordfish and their eggs. Examples of invertebrate protein sources include lobster, crab, clams, mussels, oysters, and combinations thereof.

Protein hydrolysates are commercially available or can be prepared using methods generally known to those of skill in the art. For example, suitable protein hydrolysates can be prepared by treating a biological source of protein with one or more enzymes such as a protease, for example trypsin or chymotrypsin; one or more non-enzyme chemical reagents, such as an acid, for example acetic acid; or some combination thereof. Hence, a protein hydrolysate can be produced by any known chemical or enzymatic method, such as, for example, methods disclosed in the following patents and publications: U.S. Pat. No. 5,589,357; U.S. Pat. No. 4,879, 131; U.S. Pat. No. 5,039,532; U.S. Pat. No. 6,403,142; U.S. Pat. No. 6,589,574; U.S. Pat. No. 6,455,273; U.S. Patent Application Publication No. 2003/0035882; and European Patent Publication No. EP 1 236 405.

A peptide source for purposes of the present invention can be naturally occurring or can be prepared by chemical synthesis, for example through synthesis of random peptide polymers using free amino acids and a coupling reagent such as 1-ethyl-3-(3-dimethylaminopropyl)carbodiimide.

In one embodiment, the peptide source is present in the composition in an amount providing a supplemental amount of from about 0.5% to about 5% by weight glutamine on a DM basis. It will be understood that glutamine in the food composition is contributed not only by the peptide source component but also by the meat component, as glutamine is a naturally occurring amino acid in substantially all proteins. However, where an amount of glutamine in the composition is specified herein, it includes only the supplemental glutamine contributed by the peptide source. In various embodiments, the supplemental glutamine content of the composition is from about 1% to about 4%, for example from about 1% to about 3%, by weight on a DM basis.

It is believed, without being bound by theory, that any free glutamine present in the peptide source will contribute little to the glutamine intake of an animal consuming the food composition of the invention because of poor stability of such free glutamine, particularly during the cooking and/or retort procedures undergone by the composition. Accordingly, in one embodiment, only a small fraction, for example no more than about 10%, no more than about 5%, no more than about 2% or no more than about 1% by weight of the glutamine in the peptide source is in the form of free glutamine.

The amount of the peptide source to be included in the food composition depends, among other factors, on the content of glutamine in the peptide source. A peptide source having relatively high stable glutamine content can be included in a lower amount than one having a lower stable glutamine content. It is generally most efficient to select a high-glutamine peptide source such as, for example, one derived from wheat gluten or one that has been enriched in glutamine, provided no more than a small fraction of the glutamine is in free form. In various embodiments the peptide source comprises at least about 10%, at least about 15%, at least about 20% or at least about 25%, for example about 30%, by weight total glutamine.

The food composition optionally comprises one or more supplemental components in addition to water, the nutritive base and the peptide source of glutamine. Such supplemental components can, in some configurations, modify the physical characteristics of the food, such as, for example, the food's firmness or texture, enhance palatability of the food, and/or act as a nutritional supplement. Examples of nutritional supplements include vitamins such as vitamin A, vitamin C, vitamin D, vitamin E, vitamin K, thiamin, riboflavin, niacin, vitamin $B_6$, folic acid, vitamin $B_{12}$, biotin and pantothenic acid; taurine; DL-methionine; choline chloride; and minerals such as calcium carbonate, sodium chloride, potassium chloride, dicalcium phosphate, sodium chloride (iodized), calcium sulfate dihydrate, magnesium oxide, zinc oxide, ferrous sulfate, manganese oxide, copper sulfate, calcium iodate, and selenium.

In another aspect, the invention provides a glutamine-supplemented food product comprising a sealed retortable container containing a food composition as described herein. In the present context, the term "glutamine-supplemented" means having a source of glutamine other than that naturally present in the meat component of the food. The term "food product" in this context means an article of manufacture or commerce comprising a container and a food composition within the container.

Any sealed retortable container can be used, including without limitation a metal can, a retortable pouch or tray, a bottle, a jar, or a laminated paperboard retortable carton (e.g., Tetra Recart™ retortable carton). Sealing should render the container airtight.

In yet another aspect, the invention provides a process for preparing a glutamine-supplemented food product.

In one step of the process, water and a nutritive base that predominantly comprises meat and carbohydrate is contacted with a peptide source of glutamine to form a wet mixture. The amount of water is sufficient to provide, in the finished product, a food composition that comprises from about 60% to about 85% by weight water. In one embodiment, the composition comprises from about 65% to about 80% by weight water, for example, about 75% by weight water. Details and options for the nutritive base and the peptide source of glutamine are as described herein. The term "contacting" or "contacted" in the present context includes any procedure that brings the recited components into contact, for example a mixing or surface application procedure.

It is believed, without being bound by theory, that pH of the wet mixture can affect bioavailability of the glutamine provided by the peptide source. The wet mixture generally has a pH of from about 2 to about 8, but lower or higher pH values can be acceptable in certain circumstances. In one embodiment, the wet mixture has a pH of from about 4 to about 7, for example about 5.5 to about 6.5.

In another step of the process, the wet mixture is heated at a temperature of from about 50° C. to about 105° C. for a time sufficient to cook the nutritive base, to form a cooked food composition. In one embodiment, the cooking temperature is from about 65° C. to about 90° C., for example from about 80° C. to about 85° C. Sufficient cooking times are generally from about 5 minutes to about 30 minutes. It will be understood that the time necessary for cooking depends, among other factors, on the nature and composition of the nutritive base, the amount of water present, the degree of tenderizing, browning and other cooking effects desired, and the cooking temperature. A longer cooking time may be needed where a lower cooking temperature is used and a shorter cooking time where a higher cooking temperature is used.

The mixing and cooking steps may be practiced by either batch or continuous processing. In an illustrative batch process, all ingredients of the composition are contacted in a mixing and cooking apparatus such as an agitating kettle to form a wet mixture. The temperature of the wet mixture in the kettle is then raised to a level and maintained for a period effective to cook the meat and carbohydrate components. In an illustrative continuous process, the ingredients are contacted in a continuous cooking unit with or without controlled temperature zones to form a wet mixture. The wet mixture is cooked at a desired temperature, with or without cycling time (reverse, forward, pause), with an agitation system moving at a rate of from about 1 to about 65 rpm.

In a further step of the process, the cooked food composition is packaged in a retortable container, for example any such container of a type mentioned herein and the container is sealed. Packaging can occur while the composition is still at an elevated temperature. In one embodiment cooking occurs at least in part within the sealed container. In another embodiment the composition is cooled or allowed to cool after cooking, before placement of the composition in the container.

In a still further step of the process, the resulting packaged composition is sterilized by a retort procedure to form the food product. Any retort procedure, or a procedure having substantially equivalent effect, can be used. In one embodiment, filled and sealed retortable containers are placed in a continuous or batch retort device and exposed to a temperature of from about 90° C. to about 120° C. for a time of from about 3 minutes to about 80 minutes. Excessively high temperatures or long exposure times can be detrimental in over-cooking the product, and temperatures below about 90° C. or exposure for less than about 3 minutes can result in incomplete sterilization and an unacceptably short shelf-life for the product. A suitable combination of temperature and exposure time can readily be established for any particular product by one of skill in the art.

In one embodiment, the food product has a shelf-life of at least about 1 month. "Shelf-life" herein refers to a period of time for which the sealed product, upon storage in ambient conditions, retains its suitability for its intended use. In various embodiments, the food product has a shelf-life of at least about 6 months, at least about 1 year, or at least about 2 years.

In yet another aspect, the invention provides a method for increasing glutamine absorption in an animal. The method comprises feeding the animal a cooked food composition as described herein. The animal can, but need not, be in need of increased glutamine absorption. For example, increased glutamine absorption may bring no immediate or certain benefit to health or wellness of the animal, but may be a good precaution in some cases.

In still another aspect, the invention provides a method for strengthening immune function of an animal in need thereof. The method comprises maintaining the animal, for an immune function strengthening effective period, on a dietary ration that comprises at least one cooked food composition of the present invention.

An animal "in need of" strengthening of immune function can be an animal wherein the immune system is compromised by any disease, disorder or injury. In various embodiments, the animal is one suffering from, one experiencing or one who has experienced one or more symptoms of at least one condition selected from the group consisting of diarrhea, inflammatory bowel disease, reduced gut function following surgery, chemotherapy, burn, fatigue, cancer, cachexia and sepsis. Practice of the method can involve maintaining the animal on a dietary ration that consists essentially of one or more glutamine-supplemented compositions as described herein. Alternatively, a glutamine-supplemented composition as described herein can be fed to the animal in addition to, or as a partial replacement of, the animal's regular food.

What constitutes an "immune function strengthening effective period" depends on the particular condition with which weakened immune function is associated, the severity of that condition, and other factors. Typically the animal should be maintained on a dietary ration having glutamine supplementation as described herein for at least about 1 week. In various embodiments, such maintenance is continued for at least about 1 month, at least about 6 months, at least about 1 year or at least about 2 years. In one embodiment, the animal is maintained on the glutamine-supplemented dietary ration for substantially the remainder of the animal's life.

The animal can be human or non-human. In various embodiments, the animal is a vertebrate, for example a fish, a bird, a reptile or a mammal. Illustratively among mammals, the animal can be a member of the order Carnivora, including without limitation canine and feline species.

In a particular embodiment, the animal is a companion animal. A "companion animal" herein is an individual animal of any species kept by a human caregiver as a pet, or any individual animal of a variety of species that have been widely domesticated as pets, including dogs (*Canis familiaris*) and cats (*Felis domesticus*), whether or not the individual animal is kept solely or partly for companionship. Thus "companion animals" herein include working dogs, farm cats kept for rodent control, etc., as well as pet dogs and cats.

Notwithstanding these illustrative embodiments, it will be understood that the methods of the invention also are generally suitable for other mammals, including non-human mammals such as non-human primates (e.g., monkeys, chimpanzees, etc.), companion and working animals (e.g., horses, etc.), farm animals (e.g., goats, sheep, pigs, cattle, etc.), and wild and zoo animals (e.g., wolves, bears, deer, etc.). The methods of the invention also are generally suitable for use with non-mammalian animals, such as companion, farm, zoo, and wild birds, (including, for example, song birds, parrots, ducks, geese, chickens, turkeys, ostriches, etc.).

In a still further aspect, the invention provides a method for increasing stability of supplemental glutamine added prior to cooking and/or sterilizing of a retortable (e.g., canned) food composition. The method comprises adding the supplemental glutamine in the form of a peptide source of glutamine as described herein.

In a still further aspect, the invention provides a means for communicating information about or instructions for feeding a cooked food composition as described herein. The means comprises a label, a brochure, an advertisement, a package insert, a computer-readable digital or optical medium, an audio presentation, a visual presentation, or one or more pages on a website, containing the information or instructions.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a method" or "a food" includes a plurality of such methods or foods. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All percentages used herein, including in the Examples, are weight percentages on a dry matter basis unless otherwise indicated.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

EXAMPLES

The invention can be further illustrated by the following examples, although it will be understood that these examples are included merely for purposes of illustration and are not intended to limit the scope of the invention unless otherwise specifically indicated.

Example 1

This example illustrates bioavailability of a stable source of glutamine obtained from a wheat gluten hydrolysate incorporated into a canned pet food product.

Twenty-four dogs were randomly assigned to one of the four groups designated as control, A, B and C. A canned pet food composition formulated to contain 0%, 1%, 2% and 4% added glutamine (from a wheat gluten hydrolysate source containing 30% glutamine) on a dry matter basis was fed to control, A, B and C groups respectively. The composition contained approximately 75% water and approximately 50% carbohydrate, 22% protein and 14% fat on a DM basis. The composition had a pH of from about 5.5 to 6.5 and was heated to 180° F. (82° C.) for cooking. The canned food underwent a retort process.

After canning and retort sterilization, the cans were stored for 10 days before being opened and their contents fed to the dogs. Thereafter, the four groups of dogs were fed the appropriate food compositions food for 21 days at maintenance level. On day 1 and day 21, plasma glutamine levels were determined at 0 (baseline), 30, 60, 120 and 180 minutes after feeding.

Glutamine in blood plasma was separated, identified, and quantified via HPLC. Samples were prepared for analysis by allowing them to reach room temperature and then diluting a portion of the sample with a deproteinizing solution (13.5% w/v 5-sulfosalicylic acid hydrate), internal standard solution (Glucosaminic Acid), and often a starting eluent Lithium buffer. The mixture was then vortexed, microcentrifuged, and filtered through a 0.2 micron filter via syringe. The samples were then stored refrigerated before being placed on an autoloader/sampler awaiting sample injection.

Amino acid analysis was performed on Beckman Instruments Models 6300 and 7300 dedicated HPLC amino acid analyzers. These instruments incorporate 10 cm cation exchange columns, four sequential lithium-based eluents, and lithium hydroxide for column regeneration. Absorbance was measured at 440 and 570 nm following post-column color development by Ninhydrin reagent at 131 degrees C. Data acquisition and management was accomplished with a computer running Beckman System Gold 8.10 chromatography software. Beckman reference solutions fulfilled standardization requirements.

As shown in Table 1, on day 1 there was an increase in plasma glutamine level 30 minutes after feeding in all the dogs in groups A, B and C, but no such increase was seen in dogs fed the control food. The increase was greater in the group receiving the 4% glutamine-supplemented food (group C) than in the groups receiving 1% or 2% glutamine supplementation. Plasma glutamine was lower than fasting (baseline measured immediately prior to feeding) at 120 minutes and 180 minutes in the group receiving the control food.

On day 21, the increase in plasma glutamine level at 30 minutes was higher than at day 1 in each of groups A-C. Plasma glutamine was higher than fasting at 30 minutes for all groups. The small increase in plasma glutamine in the control group suggests that the food fed was adequate in glutamine, while the greater increase with glutamine supplementation showed that the supplementary glutamine was able to be absorbed. Furthermore, the 30 minute increases in plasma glutamine in groups A-C were all similar at day 21, suggesting that equilibrium may have occurred and that long term supplementation of 1% glutamine may be sufficient to maintain a healthy glutamine status.

TABLE 1

Change Over Baseline in Plasma Glutamine Levels

| Group | Day | Plasma glutamine level, relative to level at 0 min | | | |
| --- | --- | --- | --- | --- | --- |
| | | 0 min | 30 min | 60 min | 120 min |
| Control | Day 1 | 1.00 | 1.01 | 0.95 | 0.86 |
| | Day 21 | 1.00 | 1.11 | 1.06 | 0.89 |
| A (1%) | Day 1 | 1.00 | 1.07 | 1.02 | 0.93 |
| | Day 21 | 1.00 | 1.22 | 1.11 | 0.91 |
| B (2%) | Day 1 | 1.00 | 1.06 | 0.99 | 0.95 |
| | Day 21 | 1.00 | 1.20 | 1.04 | 0.97 |
| C (4%) | Day 1 | 1.00 | 1.10 | 1.06 | 0.98 |
| | Day 21 | 1.00 | 1.19 | 1.12 | 1.11 |

These data demonstrate that a stable source of glutamine obtained from a hydrolysate can be incorporated into a canned pet food product, where it is bioavailable to animals consuming the food, even where the food has undergone conditions such as, for example, high heat and pressure for cooking and sterilization.

Example 2

This example illustrates bioavailability of glutamine obtained from different gluten hydrolysate sources.

Three different wheat gluten hydrolysates (groups designated as H1, H2 and H3) and one soy gluten hydrolysate (H4) were incorporated in a dry pet food to determine if there were differences in the availability of the glutamine for absorption. Five dogs were fed each of the foods containing H1-H4 and plasma glutamine levels were determined. Dogs in a control group were fed a dry pet food that was not supplemented with a gluten hydrolysate source. All dogs were fed early in the morning with blood drawn before feeding, and at 30, 60 and 120 minutes after feeding.

As shown in Table 2, all four gluten hydrolysate sources (groups H1-H4) showed absorption of glutamine at 30 and 60 minutes after feeding.

The three wheat gluten hydrolysate sources (H1-H3) showed comparable glutamine availability for absorption while the soy gluten hydrolysate source (H4) showed a slightly lower absorption of glutamine. Nevertheless, plasma glutamine in the dogs in each of groups H1-H4 were higher than control.

TABLE 2

Change Over Baseline in Plasma Glutamine Levels

| | Plasma glutamine level, relative to level at 0 min | | | |
|---|---|---|---|---|
| Group | 0 min | 30 min | 60 min | 120 min |
| Control | 1.00 | 0.98 | 0.99 | 0.94 |
| H1 | 1.00 | 1.13 | 1.03 | 0.91 |
| H2 | 1.00 | 1.08 | 1.10 | 1.07 |
| H3 | 1.00 | 1.09 | 1.11 | 0.93 |
| H4 | 1.00 | 1.04 | 0.93 | 0.91 |

Example 3

This example illustrates that conditions used in preparing pet foods can be destructive to free glutamine.

To determine if free glutamine can be used in the same manner to supply glutamine to the animal, free L-glutamine was incorporated into a canned pet food at 1% and 2% (Can 1 and Can 2 respectively). The food was heated to 180° F. (82° C.) for cooking and the canned food underwent a retort process.

Resulting free glutamine was measured in the final food product using a calorimetric method based on the formation of formazan due to the reaction between L-glutamate and NAD (nicotinamide adenine dinucleotide). Formazan is measured in the visible range of 492 nm. The reaction was used to measure L glutamine after L-glutamic acid was completely used up in the original reaction. Then glutaminase was added to the food sample to convert glutamine to glutamate and the reaction repeated, this time to measure only glutamate that was converted from glutamine.

As shown in Table 3, free glutamine was undetectable in the canned pet foods (Can 1 and Can 2). In contrast, when free glutamine was added to dry pet foods (Dry 1-4 as indicated in the table), recovery of free glutamine was about 62% to about 86%, indicating that, by comparison, the canning process is highly destructive to free glutamine.

TABLE 3

Stability of Free Glutamine in Dry Versus Canned Food

| | % Free glutamine (DM basis) | |
|---|---|---|
| Food | Added | Recovered |
| Dry 1 | 0 | not detected |
| Dry 2 | 0 | 0.46 |
| Dry 3 | 2 | 1.24 |
| Dry 4 | 2 | 1.71 |
| Can 1 | 1 | not detected |
| Can 2 | 2 | not detected |

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A retorted pet food composition, consisting of:
   a wet mixture heated at a temperature from about 50° C. to about 105° C. for a time sufficient to cook a nutritive base of the pet food composition;
   wherein the wet mixture consists of:
      an amount of water sufficient to provide the pet food composition with water in an amount of from about 60% by weight to about 85% by weight;
      the nutritive base; and
      a peptide source of glutamine comprising polypeptides and one or more of a partially hydrolyzed starch, a cellulose, and a partially hydrolyzed cellulose, wherein a weight average molecular weight of the polypeptides is no greater than about 12 kd;
   wherein the wet mixture has a pH greater than or equal to 5.5 and less than or equal to 6.5; and
   wherein the nutritive base comprises greater than 75% meat and carbohydrate, by weight of the nutritive base.

2. The food composition of claim 1, wherein the wet mixture is heated at a temperature from about 65° C. to about 90° C. for a time sufficient to cook the nutritive base of the pet food composition.

3. The food composition of claim 1, wherein the wet mixture is heated at a temperature from about 80° C. to about 85° C. for a time sufficient to cook the nutritive base of the pet food composition.

4. The food composition of claim 1, wherein the wet mixture has a pH of 5.5.

5. The food composition of claim 1, wherein the wet mixture has a pH of 6.5.

6. The food composition of claim 1, wherein the amount of water present is sufficient to provide the food composition with water in the amount of from about 65% by weight to about 80% by weight.

7. The food composition of claim 1, wherein the amount of water present is sufficient to provide the food composition with water in the amount of about 60% by weight.

8. The food composition of claim 1, wherein the amount of water present is sufficient to provide the food composition with water in the amount of about 65% by weight.

9. The food composition of claim 1, wherein the amount of water present is sufficient to provide the food composition with water in the amount of about 75% by weight.

10. The food composition of claim 1, wherein the amount of water present is sufficient to provide the food composition with water in the amount of about 80% by weight.

11. The food composition of claim 1, wherein the amount of water present is sufficient to provide the food composition with water in the amount of about 85% by weight.

12. The food composition of claim 1, wherein a glutamine content contributed by the peptide source of glutamine is from about 0.5% to about 5% by weight of the food composition on the dry matter basis.

13. The food composition of claim 1, wherein a glutamine content contributed by the peptide source of glutamine is from about 1% to about 4% by weight of the food composition on the dry matter basis.

14. The food composition of claim 1, wherein no more than about 2% by weight of the glutamine in the peptide source of glutamine is in a form of free glutamine.

15. The food composition of claim 1, wherein no more than about 1% by weight of the glutamine in the peptide source of glutamine is in a form of free glutamine.

16. The food composition of claim 1, wherein the peptide source of glutamine further comprises a protein hydrolysate.

17. The food composition of claim 16, wherein the protein hydrolysate is derived at least in part from a plant source.

18. The food composition of claim 16, wherein the protein hydrolysate is derived at least in part from barley, oat, rye, triticale, wheat, soy, or combinations thereof.

19. The food composition of claim 16, wherein the protein hydrolysate is derived at least in part from an animal source.

20. The food composition of claim 16, wherein the protein hydrolysate is derived at least in part from a mammal source, an avian source, a reptilian source, an amphibian source, a fish source, an invertebrate source, or combinations thereof.

21. A glutamine-supplemented food product comprising a sealed retortable container containing the food composition of claim 1.

22. The food product of claim 21, wherein the container is a metal can, a retortable pouch, a retortable tray, a bottle, a jar, or a laminated paperboard retortable carton.

23. A device configured to communicate information about or instructions for feeding the food composition of claim 1 to an animal, comprising: a label, a brochure, an advertisement, a package insert, a computer-readable digital or optical medium, an audio presentation, a visual presentation, or one or more pages on a website, containing the information or the instructions.

24. The food composition of claim 1, wherein the peptide source further comprises one or more organic oils.

25. The food composition of claim 24, wherein the organic oils comprises one or more of soybean oil, safflower oil, palm oil, coconut oil, sunflower oil, peanut oil, and canola oil.

\* \* \* \* \*